United States Patent
Berry et al.

(10) Patent No.: US 6,887,984 B2
(45) Date of Patent: May 3, 2005

(54) PROCESSES AND ORGANISMS FOR THE PRODUCTION OF ANTI-FREEZE PROTEINS

(75) Inventors: Mark John Berry, Bedford (GB); Allen Griffiths, Bedford (GB); Philip John Hill, Nottingham (GB); Johanna Laybourne-Parry, East Leake (GB); Sarah Victoria Mills, Glasgow (GB)

(73) Assignee: Good Humor-Breyers Ice Cream, a division of Conopco, Inc., Green Bay, WI (US)

( * ) Notice: Subject to any disclaimer, the term of this patent is extended or adjusted under 35 U.S.C. 154(b) by 441 days.

(21) Appl. No.: 09/737,297

(22) Filed: Dec. 15, 2000

(65) Prior Publication Data

US 2002/0072108 A1 Jun. 13, 2002

(30) Foreign Application Priority Data

Dec. 15, 1999 (GB) .............................................. 9929696

(51) Int. Cl.[7] .......................... C07K 14/00; C07K 1/00; A61K 38/00; A23J 1/00; A23J 1/02
(52) U.S. Cl. ...................... 530/825; 530/300; 530/326; 530/395; 426/656; 426/657
(58) Field of Search ............................... 530/300, 326, 530/395, 825; 426/656, 657

(56) References Cited

FOREIGN PATENT DOCUMENTS

| WO | 97/02343 | 1/1997 |
|---|---|---|
| WO | 98/04146 | 2/1998 |
| WO | 98/04148 | 2/1998 |
| WO | 99/37782 | 7/1999 |

OTHER PUBLICATIONS

International Search Report (PCT/EP 00/12396)—search completion date of Nov. 30, 2001.
XP–000676918 ("An Antifreeze Glycopeptide Gene From The Antarctic Cod *Notothenia Coriiceps Neglecta* Encodes A Polyprotein Of High Peptide Copy Number", *Proc. Natl. Acad. Sci. USA*, vol. 87, pp. 9265–9269, Dec. 1990).
XP–001012989 ("Low Temperature Growth, Freezing Survival, and Production Of Antifreeze Protein By The Plant Growth Promoting Rhizobacterium *Pseudomonas Putida* GR12–2", X. Sun, M. Griffith, J.J. Paternak and B.R. Glick, *Can J. Microbiol.*, 41: 776–784, (1995)).
XP–002174447 ("*Marinomonas Protea* Sp. Nov., A Novel Antarctic Bacterium Isolated From Ace Lake, Eastern Antarctica", Mills S.V., Stewart G.S.A.B., Laybourn–Parry J., Hill P.J., May 3, 1999)—abstract to Seq. ID No. 1.
XP–002184397 ("*Pseudomonas Libanienses* 16S Ribosomal RNA Gene, Complete Sequence", Dabboussi et al., Apr. 16, 1998)—abstract to Seq. ID No. 2.
XP–002184397 ("Microbial Diversity In Sediments Collected From The Deepest Cold–Seep Area, The Japan Trench", Li et al., Jun. 22, 1998)—abstract to Seq. ID No. 2.
"Biomechanics—Materials. A Practical Approach", Ed. J.F.V. Vincent, Pub. IRL Press, Oxford University Press, Walton Street, Oxford, 1992.
"Antifreeze Proteins and Their Potential Use In Frozen Foods", *Biotechnology Advances*, vol. 13, No. 3, pp. 375–402.
"Isolation And Characterization Of An Antifreeze Protein With Ice Nucleation Activity From The Plant Growth Promoting Rhizobacterium *Pseudomonas Putida* GR12–2", *Can. J. Microbiol.*, 44: 64–73, (1998).
"Handbook of Plastics Test Methods", Ed. R.P. Brown, Pub. George Godwin Limited, The Builder Group, pp. 112–121, Pemberton Row, Fleet Street, London (1981).

*Primary Examiner*—Jon Weber
*Assistant Examiner*—Rita Mitra
(74) *Attorney, Agent, or Firm*—Gerard J. McGowan, Jr.

(57) ABSTRACT

The invention relates to a process for preparing an anti-freeze peptide and to the peptides obtained from bacteria from an aqueous low-temperature environment, such as *Marinomonas protea* and a *Pseudomonas* species. These anti-freeze peptides can suitably be incorporated in frozen food products such as frozen vegetables and frozen confectionery such as ice-cream.

8 Claims, 13 Drawing Sheets

Fig.1.

```
             1                                                          60
196x.seq     GT................TAGCTCAGATTGAACGCTGGCGGCAGGCTTAAACACATGC
Mcomm.seq    NAAACTGAAGAGTTTGATCATGGCTCAGATTGAACGCTGGCGGCAGGCTTAA.CACATGC 61                                                         120
196x.seq     AAGTCGAGCGGTAACAGGGG.AGCTTGCTCCT.GCTGACGAGCGGCGGACGGGTGAGTAA
Mcomm.seq    AAGTCGAGCGGTAACATTGCTAGCTTGCTAGAAGATGACGAGCGGCGGACGGGTGAGTAA 121                                                        180
196x.seq     CGCGTAGGAATCTGCCTAGTAGAGGGGGACAACATGTGGAAACGCATGCTAATACCGCAT
Mcomm.seq    CGCGTAGGAATCTGCCTAGTAGTGGGGGACAACATGTGGAAACGCATGCTAATACCGCAT 181                                                        240
196x.seq     ACGCCCTGAGGGGGAAAGGAGGGGACTCTTCGGAGCCTTCCGCTATTAGATGAGCCTGCG
Mcomm.seq    ACGCCCTACGGGGGAAAGGAGGGNN.TCTTCGGA.CCTTTCGCTATTAGATGAGCCTGCG 241                                                        300
196x.seq     TGAGATTAGCTAGTTGGTAGGGTAAAGGCCTACCAAGGCGACGATCTCTAACTGGTCTGA
Mcomm.seq    TGAGATTAGCTAGTTGGTGGGGTAAAGGCCTACCAAGGCGACGATCTCTAGCTGGTCTGA 301                                                        360
196x.seq     GAGGATGACCAGTCACACTGGGACTGAGACACGGCCCAGACTCCTACGGGAGGCAGCAGT
Mcomm.seq    GAGGATGATCAGCCACACTGGGACTGAGACACGGCCCAGACTCCTACGGGAGGCAGCAGT 361                                                        420
196x.seq     GGGGAATATTGGACAATGGGCGCAAGCCTGATCCAGCCATGCCGCGTGTGTGAAGAAGGC
Mcomm.seq    GGGGAATATTGGACAATGGGCGCAAGCCTGATCCAGCCATGCCGCGTGTGTGAAGAAGGC 421                                                        480
196x.seq     CTTAGGGTTGTAAAGCACTTTCAGGGGTGAGGAAGGGTGATAGGTTAATACGTTATCATC
Mcomm.seq    CTTAGGGTTGTAAAGCACTTTCAGGAGTGAGGAAGGGCGTATAGTTAATACCTGTATGTT 481                                                        540
196x.seq     TTGACGTTAGCCCCAGAAGAAGCACCGGCTAACTCTGTGCCAGCAGCCGCGGTAATACAG
Mcomm.seq    TTGACGTTAACTCCAGAAGAAGCACCGGCTAACTCTGTGCCAGCAGCCGCGGTAATACAG 541                                                        600
196x.seq     AGGGTGCAAGCGTTAATCGGAATTACTGGGCGTAAAGCGCGCGTAGGTGGTTTGTTAAGT
Mcomm.seq    AGGGTGCGAGCGTTAATCGGAATTACTGGGCGTAAAGCGCGCGTAGGCGGTTTGTTAAGT 601                                                        660
196x.seq     CGGATGTGAAATCCCAGGGCTCAACCTTGGAATGGCACCCGATACTGGCTAGCTAGAGTA
Mcomm.seq    CGGATGTGAAATCCCAGGGCTCAACCTTGGAATGGCACCCGATACTGGCAGGCTAGAGTA 661                                                        720
196x.seq     TGGTAGAGGGGTGTGGAATTTCCTGTGTAGCGGTGAAATGCGTAGATATAGGAAGGAACA
Mcomm.seq    CGGTAGAGGGGTGTGGAATTTCCTGTGTAGCGGTGAAATGCGTAGATATAGGAAGGAACA 721                                                        780
196x.seq     TCAGTGGCGAAGGCGACACCCTGGACTAATACTGACACTGAGGTGCGAAAGCGTGGGGAG
Mcomm.seq    TCAGTGGCGAAGGCGACACCCTGGACCGATACTGACGCTGAGGTGCGAAAGCGTGGGGAG 781                                                        840
196x.seq     CAAACAGGATTAGATACCCTGGTAGTCCACGCCGTAAACGATGTCTACTAGCCGTTGGGT
Mcomm.seq    CAAACAGGATTAGATACCCTGGTAGTCCACGCCGTAAACGATGTCTACTAGCCGTTGGGG 841                                                        900
196x.seq     .TGTAATGACTTAGTGGCGCAGCTAACGCAATAAGTAGACCGCCTGGGGAGTACGGCCGC
Mcomm.seq    ATNTATTTCTTTAGTGGCGCAGCTAACGCGATAAGTAGACCGCCTGGGGAGTACGGCCGC 901                                                        960
196x.seq     AAGGTTAAAACTCAAATGAATTGACGGGGGCCCGCACAAGCGGTGGAGCATGTGGTTTAA
Mcomm.seq    AAGGTTAAAACTCAAATGAATTGACGGGGGCCCGCACAAGCGGTGGAGCATGTGGTTTAA 961                                                        1020
196x.seq     TTCGAAGCAACGCGAAGAACCTTACCTACTCTTGACATCCACAGAACATTTGAGAGATCA
Mcomm.seq    TTCGAANNAACGCGAAGAACCTTACCTACTCTTGACATCCAGAGAACTTTYCAGAGATGA
```

Fig.1(cont.)

```
              1021                                                          1080
196x.seq     GATGGTGCCTTCGGGAACTGTGAGACAGGTGCTGCATGGCTGTCGTCAGCTCGTGTTGTG
Mcomm.seq    ATTGGTGCCTTCGGGAACTCTGAGACAGGTGCTGCATGGCTGTCGTCAGCTCGTGTTGTG 1081                                                          1140
196x.seq     AAATGTTGGGTTAAGTCCCGTAACGAGCGCAACCCTTGTCCTTATTTGCCAGCACGTAAT
Mcomm.seq    AAATGTTGGGTTAAGTCCCGTAACGAGCGCAACCCTTATCCTTATTTGCCAGCACTTCG.

1141                                                          1200
196x.seq     GGTGGGAACTTTAAGGAGACTGCCGGTGACAAACCGGAGGAAGGTGGGGACGACGTCAAG
Mcomm.seq    GGTGGNAACTCTAAGGAGACTGCCGGTGACAAACCGGAGGAAGGTNGGNNCGACGTCAAG 1201                                                          1260
196x.seq     TCATCATGGCCCTTACGAGTAGGGCTACACACGTGCTACAATGGCGTATACAGAGGGCTG
Mcomm.seq    TCATCATGGCCCTTACGAGTAGGGCTACACACGTGCTACAATGGCGTATACAGAGGGCAG 1261                                                          1320
196x.seq     CAAGCTAGCGATAGTGAGCGAATCCCACAAAGTACGTCGTAGTCCGGATTGGAGTCTGCA
Mcomm.seq    CGAACTCGCGAGGGTAAGCAAATCCCAAAAAGTACGTCGTAGTCCGGATTGGAGTCTGCA 1321                                                          1380
196x.seq     ACTCGACTCCATGAAGTCGGAATCGCTAGTAATCGTGAATCAGAATGTCACGGTGAATAC
Mcomm.seq    ACTCGACTCCATGAAGTCGGAATCGCTAGTAATCGTGAATCAGAATGTCACGGTGAATAC 1381                                                          1440
196x.seq     GTTCCCGGGCCTTGTACACACCGCCCGTCACACCATGGGAGTTGATTGCTCCAGAAGTAG
Mcomm.seq    GTTCCCGGGCCTTGTACACACCGCCCGTCACACCATGGGAGTTGATTGCTCCAGAAGTAG 1441                                                          1500
196x.seq     CTAGCTTAACCCTTCGGGGATGGCGGTTACCACGGAGTGGTCAATGACTGGGGTTGAAGT
Mcomm.seq    CTAGCTTAACCTNC..GGGATGGCGGTTACCACGGAGTGGTCAATGA.............

1501
196x.seq     CTACGCG
Mcomm.seq    .......
```

Fig.3.

```
  1 GCCCTTGCTCAGATTGAACGCTGGCGGCAGGCCT.AACACATGCAAGTCG  49
    | ||||||||||||||||||||||||||||| | |||||||||||||||
  1 ..gttagctcagattgaacgctggcggcaggcttaaacacatgcaagtcg  48

50 AGCGGT.AGAGAGAAGCTTGCTTCTCTTGA.GAGCGGCGGACGGGTGAGT  97
    |||||| | || | |||||||| || ||| |||||||||||||||||||
 49 agcggtaacaggggagcttgctcctgctgacgagcggcggacgggtgagt  98

98 AATGCCTAGGAATCTGCCTGGTAGTGGGGGATAACGTTCGGAAACGGACG 147
    || || |||||||||||| |||| |||||| ||| | |||||| | |
 99 aacgcgtaggaatctgcctagtagaggggGacaacatgtggaaacgcatg 148

148 CTAATACCGCATACGTCCTACGGGAGAAAGCAGGGA..CCTTCGGGCCT  195
    |||||||||||| ||| ||| ||||| ||||||  | |  | ||||
149 ctaataccgcatacgccctgagggggaaggagGggactcttcggagcct  198

196 TGCGCTATCAGATGAGCCTAGGTCGGATTAGCTAGTTGGTGAGGTAATGG 245
    | |||||| ||||||||| || ||||||||||||||| ||||| ||
199 tccgctattagatgagcctgcgtgagattagctagttggtagggtaaagg 248

246 CTCACCAAGGCGACGATCCGTAACTGGTCTGAGAGGATGATCAGTCACAC 295
    |  |||||||||||||||  |||||||||||||||||||| ||||||||
249 cctaccaaggcgacgatctctaactggtctgagaggatgaccagtcacac 298

296 TGGAACTGAGACACGGTCCAGACTCCTACGGGAGGCAGCAGTGGGGAATA 345
    ||| ||||||||||| ||||||||||||||||||||||||||||||||||
299 tgggactgagacacggcccagactcctacgggaggcagcagtggggaata 348

346 TTGGACAATGGGCGAAAGCCTGATCCAGCCATGCCGCGTGTGTGAAGAAG 395
    ||||||||||||| |||||||||||||||||||||||||||||||||||
349 ttggacaatgggcgcaagcctgatccagccatgccgcgtgtgtgaagaag 398

396 GTCTTCGGATTGTAAAGCACTTTAAGTTGGGAGGAAGGGTTGTAGATTAA 445
    | ||| || ||||||||||||| || | ||||||||| |||  |||
399 gccttaggggttgtaaagcactttcaggggtgaggaagggtgataggttaa 448

446 TACTCTGCAATTTTGACGTTACCGACAGAATAAGCACCGGCTAACTCTGT 495
    ||| |   ||  ||||||||| |  |||| |||||||||||||||||||
449 tacgttatcatcttgacgttagccccagaagaagcaccggctaactctgt 498
```

Fig.3(cont.)i

```
496 GCCAGCAGCCGCGGTAATACAGAGGGTGCAAGCGTTAATCGGAATTACTG 545
    ||||||||||||||||||||||||||||||||||||||||||||||||||
499 gccagcagccgcggtaatacagagggtgcaagcgttaatcggaattactg 548

546 GGCGTAAAGCGCGCGTAGGTGGTTTGTTAAGTTGGATGTGAAATCCCCGG 595
    |||||||||||||||||||||||||||||| |||||||||||||||| ||
549 ggcgtaaagcgcgcgtaggtggtttgttaagtcggatgtgaaatcccagg 598

596 GCTCAACCTGGGAACTGCATTCAAAACTGACTGACTAGAGTATGGTAGAG 645
    |||||||| |||| ||| | | |||| ||  |||||||||||||||||
599 gctcaaccttggaatggcacccgatactggctagctagagtatggtagag 648

646 GGTGGTGGAATTTCCTGTGTAGCGGTGAAATGCGTAGATATAGGAAGGAA 695
    ||  ||||||||||||||||||||||||||||||||||||||||||||||
649 gggtgtggaatttcctgtgtagcggtgaaatgcgtagatataggaaggaa 698

696 CACCAGTGGCGAAGGCGACCACCTGGACTAATACTGACACTGAGGTGCGA 745
    || |||||||||||||||   |||||||||||||||||||||||||||||
699 catcagtggcgaaggcgacaccctggactaatactgacactgaggtgcga 748

746 AAGCGTGGGGAGCAAACAGGATTAGATACCCTGGTAGTCCACGCCGTAAA 795
    ||||||||||||||||||||||||||||||||||||||||||||||||||
749 aagcgtggggagcaaacaggattagataccctggtagtccacgccgtaaa 798
```

Fig.3(cont.)ii

```
796  CGATGTCAACTAGCCGTTGGAAGCCTTGAGCTTTTAGTGGCGCAGCTAAC  845
     |||||||  ||||||||||| |   | |      ||||||||||||||||
799  cgatgtctactagccgttgg..gttgtaatgacttagtggcgcagctaac  846

846  GCATTAAGTTGACCGCCTGGGGAGTACGGCCGCAAGGTTAAAACTCAAAT  895
     |||  |||||  ||||||||||||||||||||||||||||||||||||||
847  gcaataagtagaccgcctggggagtacggccgcaaggttaaaactcaaat  896

896  GAATTGACGGGGGCCCGCACAAGCGGTGGAGCATGTGGTTTAATTCGAAG  945
     ||||||||||||||||||||||||||||||||||||||||||||||||||
897  gaattgacgggggcccgcacaagcggtggagcatgtggtttaattcgaag  946

946  CAACGCGAAGAACCTTACCAGGCCTTGACATCCAATGAACTTTCTAGAGA  995
     |||||||||||||||||||    |||||||||| |||| ||    |||||
947  caacgcgaagaaccttacctactcttgacatccacagaacatttgagaga  996

996  TAGATTGGTGCCTTCGGGAACATTGAGACAGGTGCTGCATGGCTGTCGTC  1045
     |    |||||||||||||| ||||||||||||||||||||||||||||||
997  tcagatggtgccttcgggaactgtgagacaggtgctgcatggctgtcgtc  1046

1046 AGCTCGTGTTGTGAAATGTAAGGGC.........................  1070
     ||||||||||||||||||||||| ||
1047 agctcgtgttgtgaaatgttgggttaagtcccgtaacgagcgcaacccctt  1096
```

Fig.4.

```
                    10         20         30         40         50
Isolate 20
                    GCCCTTGCTCAGATTGAACGCTGGCGGCAGGCCTAACACATGCAAGTCGAGC
             :  :  ::::::::::::::::::::::::::::::::::::::::::::::::
P.synx  AGAGTTTGATCTTGGCTCAGATTGAACGCTGGCGGCAGGCCTAACACATGCAAGTCGAGC
            10         20         30         40         50         60

60         70         80         90        100        110
        GGTAGAGAGAAGCTTGCTTCTCTTGAGAGCGGCGGACGGGTGAGTAATGCCTAGGAATCT
        ::::::::::::::::::::::::::::::::::::::::::::::::::::::::::::
        GGTAGAGAGAAGCTTGCTTCTCTTGAGAGCGGCGGACGGGTGAGTAATGCCTAGGAATCT
            70         80         90        100        110        120

120        130        140        150        160        170
        GCCTGGTAGTGGGGGATAACGTTCGGAAACGGACGCTAATACCGCATACGTCCTACGGGA
        ::::::::::::::::::::::::::::::::::::::::::::::::::::::::::::
        GCCTGGTAGTGGGGGATAACGTTCGGAAACGGACGCTAATACCGCATACGTCCTACGGGA
           130        140        150        160        170        180

180        190        200        210        220        230
        GAAAGCAGGGGACCTTCGGGCCTTGCGCTATCAGATGAGCCTAGGTCGGATTAGCTAGTT
        ::::::::::::::::::::::::::::::::::::::::::::::::::::::::::::
        GAAAGCAGGGGACCTTCGGGCCTTGCGCTATCAGATGAGCCTAGGTCGGATTAGCTAGTT
           190        200        210        220        230        240

240        250        260        270        280        290
        GGTGAGGTAATGGCTCACCAAGGCGACGATCCGTAACTGGTCTGAGAGGATGATCAGTCA
        ::::::::::::::::::::::::::::::::::::::::::::::::::::::::::::
        GGTGAGGTAATGGCTCACCAAGGCGACGATCCGTAACTGGTCTGAGAGGATGATCAGTCA
           250        260        270        280        290        300

300        310        320        330        340        350
        CACTGGAACTGAGACACGGTCCAGACTCCTACGGGAGGCAGCAGTGGGGAATATTGGACA
        ::::::::::::::::::::::::::::::::::::::::::::::::::::::::::::
        CACTGGAACTGAGACACGGTCCAGACTCCTACGGGAGGCAGCAGTGGGGAATATTGGACA
           310        320        330        340        350        360

360        370        380        390        400        410
        ATGGGCGAAAGCCTGATCCAGCCATGCCGCGTGTGTGAAGAAGGTCTTCGGATTGTAAAG
        ::::::::::::::::::::::::::::::::::::::::::::::::::::::::::::
        ATGGGCGAAAGCCTGATCCAGCCATGCCGCGTGTGTGAAGAAGGTCTTCGGATTGTAAAG
           370        380        390        400        410        420

420        430        440        450        460        470
        CACTTTAAGTTGGGAGGAAGGGTTGTAGATTAATACTCTGCAATTTTGACGTTACCGACA
        ::::::::::::::::::::::::::::::::::::::::::::::::::::::::::::
        CACTTTAAGTTGGGAGGAAGGGTTGTAGATTAATACTCTGCAATTTTGACGTTACCGACA
           430        440        450        460        470        480
```

Fig.4(cont.)i

```
           480       490       500       510       520       530
    GAATAAGCACCGGCTAACTCTGTGCCAGCAGCCGCGGTAATACAGAGGGTGCAAGCGTTA
    ::::::::::::::::::::::::::::::::::::::::::::::::::::::::::::
    GAATAAGCACCGGCTAACTCTGTGCCAGCAGCCGCGGTAATACAGAGGGTGCAAGCGTTA
           490       500       510       520       530       540

540       550       560       570       580       590
    ATCGGAATTACTGGGCGTAAAGCGCGCGTAGGTGGTTTGTTAAGTTGGATGTGAAATCCC
    ::::::::::::::::::::::::::::::::::::::::::::::::::::::::::::
    ATCGGAATTACTGGGCGTAAAGCGCGCGTAGGTGGTTTGTTAAGTTGGATGTGAAATCCC
           550       560       570       580       590       600

600       610       620       630       640       650
    CGGGCTCAACCTGGGAACTGCATTCAAAACTGACTGACTAGAGTATGGTAGAGGGTGGTG
    ::::::::::::::::::::::::::::::::::::::::::::::::::::::::::::
    CGGGCTCAACCTGGGAACTGCATTCAAAACTGACTGACTAGAGTATGGTAGAGGGTGGTG
           610       620       630       640       650       660

660       670       680       690       700       710
    GAATTTCCTGTGTAGCGGTGAAATGCGTAGATATAGGAAGGAACACCAGTGGCGAAGGCG
    ::::::::::::::::::::::::::::::::::::::::::::::::::::::::::::
    GAATTTCCTGTGTAGCGGTGAAATGCGTAGATATAGGAAGGAACACCAGTGGCGAAGGCG
           670       680       690       700       710       720

720       730       740       750       760       770
    ACCACCTGGACTAATACTGACACTGAGGTGCGAAAGCGTGGGGAGCAAACAGGATTAGAT
    ::::::::::::::::::::::::::::::::::::::::::::::::::::::::::::
    ACCACCTGGACTAATACTGACACTGAGGTGCGAAAGCGTGGGGAGCAAACAGGATTAGAT
           730       740       750       760       770       780

780       790       800       810       820       830
    ACCCTGGTAGTCCACGCCGTAAACGATGTCAACTAGCCGTTGGAAGCCTTGAGCTTTTAG
    ::::::::::::::::::::::::::::::::::::::::::::::::::::::::::::
    ACCCTGGTAGTCCACGCCGTAAACGATGTCAACTAGCCGTTGGAAGCCTTGAGCTTTTAG
           790       800       810       820       830       840

840       850       860       870       880       890
    TGGCGCAGCTAACGCATTAAGTTGACCGCCTGGGGAGTACGGCCGCAAGGTTAAAACTCA
    ::::::::::::::::::::::::::::::::::::::::::::::::::::::::::::
    TGGCGCAGCTAACGCATTAAGTTGACCGCCTGGGGAGTACGGCCGCAAGGTTAAAACTCA
           850       860       870       880       890       900

900       910       920       930       940       950
    AATGAATTGACGGGGGCCCGCACAAGCGGTGGAGCATGTGGTTTAATTCGAAGCAACGCG
    ::::::::::::::::::::::::::::::::::::::::::::::::::::::::::::
    AATGAATTGACGGGGGCCCGCACAAGCGGTGGAGCATGTGGTTTAATTCGAAGCAACGCG
           910       920       930       940       950       960

960       970       980       990      1000      1010
    AAGAACCTTACCAGGCCTTGACATCCAATGAACTTTCTAGAGATAGATTGGTGCCTTCGG
    ::::::::::::::::::::::::::::::::::::::::::::::::::::::::::::
    AAGAACCTTACCAGGCCTTGACATCCAATGAACTTTCTAGAGATAGATTGGTGCCTTCGG
           970       980       990      1000      1010      1020
```

Fig.4(cont.)ii

```
          1020       1030       1040       1050       1060       1070
       GAACATTGAGACAGGTGCTGCATGGCTGTCGTCAGCTCGTGTTGTGAAATGTAAGGGC
       ::::::::::::::::::::::::::::::::::::::::::::  ::::  ::::  ::
       GAACATTGAGACAGGTGCTGCATGGCTGTCGTCAGCTCGTGTCGTGAGATGTTGGGTTAA
          1030       1040       1050       1060       1070       1080

GTCCCGTAACGAGCGCAACCCTTGTCCTTAGTTACCAGCACGTAATGGTGGGCACTCTAA
          1090       1100       1110       1120       1130       1140
```

Span (S)   30mm
Depth (D)  ~2mm
Width (B)  10mm

PROCESSES AND ORGANISMS FOR THE PRODUCTION OF ANTI-FREEZE PROTEINS

This application claims benefit of a foreign (United Kingdom) application 9929696.4 filed on Dec. 15, 1999.

FIELD OF THE INVENTION

The present invention relates to a process for the production of anti-freeze proteins. It further relates to novel organisms useful in the process, to novel proteins obtained thereby and to compositions and uses of such novel proteins. In one aspect, it relates to cultures of the novel organism *Marinomonas protea*; to novel anti-freeze proteins derived therefrom; to the use of such proteins in controlling freezing processes, especially in the production of frozen food; and the foods thereby obtained.

BACKGROUND OF THE INVENTION

So-called 'anti-freeze proteins' (AFPs) have the property of modifying the growth of ice crystals. They differ in their action from simpler ionic anti-freeze agents such as common salt. For example, aqueous AFP solutions typically have a freezing point that is lower than their melting point (hysteresis). They stabilise ice crystals over a range of temperatures, and inhibit re-crystallisation. They seem to assist organisms to survive in temperatures around the freezing point of water, and are accordingly found in several different types of organism. Their properties give them a range of potential uses: in particular in foods that are eaten while frozen, by inhibiting recrystallisation and maintaining a smooth texture. In foods that are frozen only for preservation, AFPs may inhibit recrystallisation during freezing, storage, transport, and thawing, thus preserving food texture by reducing cellular damage and also minimising the loss of nutrients by reducing drip (see Griffith, M. and Vanya Ewart, K. *Biotechnology Advances*, 13, pp 375–402).

Various sources of AFPs are known: the commonest are fish and plants. Some bacteria exhibit anti-freeze properties (see Griffith et al, supra, p 382). In a few cases, the isolation of anti-freeze proteins from bacteria has been reported (see for example: Xu H, Griffith M, Patten CL, et al., Can J Microbiol 44: (1) 64–73 January 1998). Given the advantages to an organism of resistance to freezing, it may be considered surprising that anti-freeze proteins are not more widely distributed in Nature and easier to find. This may be because organisms have other ways of overcoming such problems.

Whereas, fish AFP that can assist production of strong, hard structures has advantages for some specialised applications, an AFP that is RI-active but does not produce hard structures has its own, different advantages. For example, molecules that actively inhibit the recrystallisation of ice upon storage may be used to maintain smooth textures of frozen products during storage. For some frozen foods, such as dairy ice cream, it would be preferable if the use of such a molecule did not harden the product excessively.

Therefore there is a desire for anti-freeze peptides which are active in recrystallisation inhibition during thawing and freezing cycles, and which can be used for maintaining smooth textures of food products during storage. Desirably these anti-freeze peptides are heat stable such that they can be incorporated in food products which are pasteurized or sterilised, while they maintain their functionality.

The hypothesis on which the present invention is (in part) based is that bacteria are more likely to evolve AFP proteins if they inhabit a liquid aqueous environment which is often below the normal freezing point of water: in such environments (it is postulated) AFPs may be an efficient way of giving bacteria a competitive advantage.

STATEMENT OF INVENTION

Accordingly, in a first aspect, the present invention consists of a process for producing AFPs which comprises collecting one or more samples of bacteria from an aqueous low-temperature environment, culturing the bacteria and extracting proteins from the samples, testing the proteins for anti-freeze properties, selecting protein having superior anti-freeze properties, and producing the selected protein in amounts sufficient for use as an AFP food additive.

The invention further comprises novel anti-freeze proteins obtainable by the process, their use in food processing, and food compositions containing them.

DETAILED DESCRIPTION OF THE INVENTION

The invention will be further described with reference to the accompanying drawings and sequence identifications, in which:

Sequence ID 1 is a DNA sequence from the 16S rRNA gene of *Marinomonas protea*;

Sequence ID 2 is a DNA sequence from the 16S rRNA gene of *Pseudomonas* species (isolated as "isolate 20").

Sequence ID 3 is the N-terminal amino acid sequence of the anti-freeze peptide isolated from *Marinomonas protea*.

FIG. 1 shows the sequence alignment of the 16S rRNA sequence of *Marinomonas protea* (SEQ ID No 1) (FIG. 3) to the corresponding sequence of *Marinomonas communis* (SEQ ID No 4);

FIG. 3 shows the 16S rRNA sequence alignment of isolate 20 (seq ID 2, upper case) to *Marinononas protea* 16S rRNA (Seq ID 1; lower case) showing 89.4% similarity.

FIG. 4 shows the 16S rRNA sequence alignment of isolate 20 (seq ID 2) to its closest phylogenetic relative *Pseudornonas synxantha* (SEQ ID No 5) showing 99.4% similarity.

Figure 7:
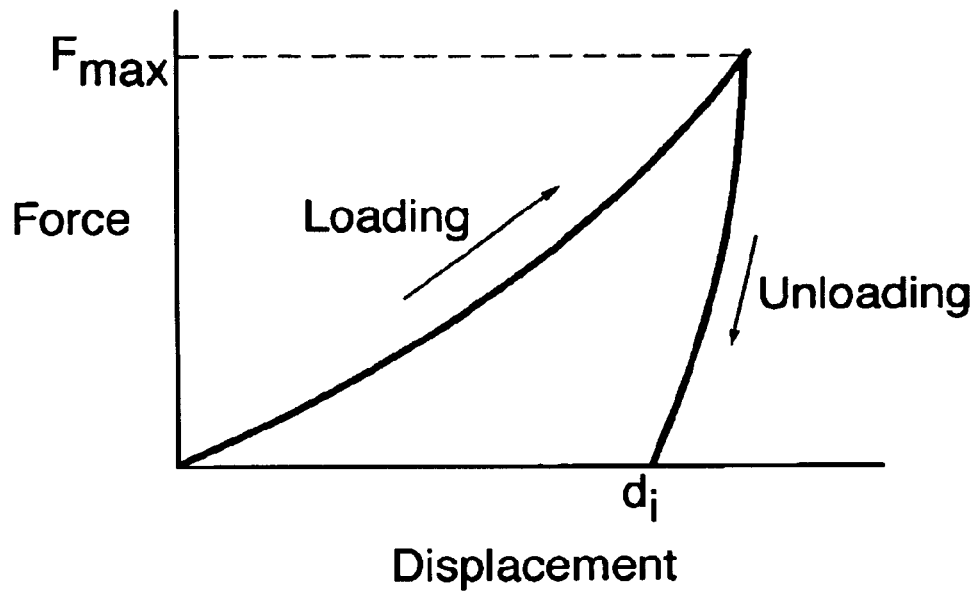

FIG. 7, 8, 9 relate to the Vickers hardness test as described in the example.

The terms anti-freeze peptide and anti-freeze protein are used interchangeably in the context of this invention. These terms are abbreviated as AFP.

By an aqueous low-temperature environment, we mean an environment comprising predominantly water that is at a temperature below 0° C. for at least part of the year. We prefer saline environments, for example having a salt content (salinity) sufficient to depress the freezing point of ice significantly (for example by 0.2° C. or more). The salinity may be more or less than that of sea water (35 ppt). Preferred environments from which bacteria can be collected are saline (including hypersaline) lakes, or loci in such lakes. In particular we prefer to collect suitable bacteria for use in the invention from Antarctic environments.

Saline lakes in Antarctica are often meromictic or monomictic. Meromictic lakes have a permanent chemically and thermally stratified water column. They have colder less saline waters above and more saline warmer waters in the depths. In Antarctica such lakes are ice-covered for most of the year, only breaking out briefly in summer. Monomictic lakes in Antarctica are hypersaline lakes, too saline to develop a proper ice-cover in winter. Ice-cover acts like a thermal blanket. Without it lake waters in contact with the air cool to very low temperatures. In winter their water columns stratify thermally, colder waters above, warmer waters below. In summer the stratification breaks down and the water column has a uniform temperature. In the case of both monomictic and meromictic Antarctic lakes there are times in winter when water temperatures are well below 0° C.

The invention further relates to novel bacterial cultures isolated from the above Antarctic lakes, preferably from meromictic or monomictic lakes.

We further provide pure bacterial cultures of *Marinomonas* species that generate anti-freeze proteins, said bacterial cultures showing at least 90% and preferably 95% homology in the 16S rRNA gene sequence with the corresponding sequence in the organism *Marinomonas protea* (Sequence ID no 1).

The invention further relates to pure bacterial cultures of *Pseudomonas* species that generate anti-freeze proteins, said bacterial cultures showing at least 90% and preferably at least 95% sequence homology in the 16S rRNA sequence with the gene sequence according to seq ID no 2. Said cultures are obtainable in the course of carrying out the process of the invention.

The process of the invention comprises four phases: collection of samples of one or more bactiera; culturing the bacteria and extraction of proteins; testing and selection of proteins; and production of proteins.

1. Collection of Samples

Samples of bacteria for use in the process of the invention are collected from aqueous low-temperature environments. As noted, by 'low temperature' environments we mean those in which ice forms for at least part of the year. Such environments occur at high altitudes and high latitudes, or both. We prefer to collect bacteria from saline environments, especially saltwater lakes. Particularly preferred environments are found in the Antarctic, and may include meromictic or monomictic lakes. Such lakes comprise loci having a variety of properties, e.g., temperatures and salt concentrations, and bacterial samples may be collected from a range of such loci for subsequent laboratory investigation.

2. Protein Extraction

Each bacterial sample is cultured under suitable conditions, such that anti-freeze protein is produced, and protein is extracted from the culture broth by standard methods, for example by centrifugation of cells, pelleting and vortexing with glass beads in the presence of buffer.

3. Testing of Proteins

Proteins extracted in stage 2 are classified by testing their anti-freeze properties. A variety of suitable tests are available. We prefer to use a recrystallisation inhibition test: as described in more detail below. This measures the tendency of ice crystals to increase in size when stored under freezing conditions in the presence of the protein. By use of this test, effective AFP proteins, in the presence of which recrystallisation and crystal growth is stopped or reduced, may be selected.

Proteins with anti-freeze properties are defined as proteins which preferably show in a recrystallisation assay as defined in the examples, an ice crystal growth of 6 $\mu$m or less at a concentration of at most 1 mg/ml.

4. Production of Proteins

Proteins selected according to the process of the invention are produced in quantity for use as AFP food additives. This may be done in a variety of ways. For example, the original process used to obtain the protein (bacterial culture followed by protein extraction) may be scaled up. By experimenting with culture conditions (temperature, media, etc.) and bacterial selection, yields may be increased. It is also possible to isolate from the bacterium the DNA sequence coding for the selected AFP, introduce it into an expression cassette and generate recombinant protein in a different host cell.

In a preferred process, the protein-containing isolate is subjected to a heat treatment such as pasteurisation or sterilisation to inactivate live bacteria and proteins which may affect the formed anti-freeze peptide such as proteases. Thus it is a very important feature of the invention that isolated AFPs are preferably resistant to heating. Without the ability to inactivate proteases by heat treatment, chemical protease-inhibitors would in many cases need to be used and most of these are toxic and therefore not compatible with use in foods.

Surprisingly the proteins isolated from the antarctic sources as indicated are heat stable, despite their natural, original environment being at very cold temperatures.

Heat stable proteins in the context of the invention are defined as proteins which show, after a pasteurisation treatment, a remaining anti-freeze activity of at least 50%, preferably at least 80% of the anti-freeze activity of the protein before the heat treatment.

Most preferred this amount of activity remains after a sterilisation treatment.

In a further aspect the invention relates to a protein showing anti-freeze properties, obtained by the process of the invention or isolated from a culture as specified above. More specifically, the invention comprises the novel protein marinomonin having anti-freeze properties. It further comprises isoforms and derivatives, e.g. glycosylated forms, of marinomonin possessing anti-freeze properties.

Most preferred these proteins show anti-freeze properties are heat stable.

As is shown in the examples the anti-freeze peptide isolated from *Marinomonas protea* shows an N-terminal amino acid sequence of Ala-Glu-Gly-Ser-Thr-Gly/Val-Asp-Val-Tyr-Gln-Asn-Ile-Gln-Tyr-Ala-Gly-(Seq ID no 3). Preferably the derivatives show at least 75%, more preferably 85% and in particular at least 95% homology in the N terminal amino acid sequence, with the 16-member peptide sequence given above.

Isoforms and derivatives of the amino acid sequence of SEQ ID no 3 having anti-freeze properties are also encompassed in the scope of the invention.

The invention further comprises nucleic acid sequences, especially DNA, encoding the novel proteins of the invention. These may readily be obtained from a knowledge of the protein sequence shown above.

In a further preferred aspect the invention relates to a nucleic acid sequence encoding the amino acid sequence of sequence ID no 3.

The process of the invention comprises culturing an organism containing a DNA sequence coding for marinomonin or another anti-freeze protein according to the invention, under conditions in which marinomonin or the anti-freeze protein is produced, and recovering this protein.

One such organism suitable for use in the invention is the newly discovered bacterium *Marinomonas protea*. Suitable conditions and media for culturing this organism are given in the examples.

Other organisms may be discovered containing DNA encoding marinomonin, which may prove useful in the process of the invention. An alternative is to employ a genetically transformed organism comprising a DNA sequence coding for an anti-freeze protein which is marinomonin or an analogue thereof, the sequence being under control of a gene promoter adapted to cause it to produce the anti-freeze protein in the transformed organism. The DNA sequence coding for the anti-freeze protein may be inserted into a suitable expression vector containing the necessary elements for transcription and translation into the desired protein under appropriate conditions, including proper orientation of the sequence, correct reading frame, and suitable targeting and expression sequences. Methods for making suitable vectors, and for using them to transform many different types of organism, are well understood in the art. Genetically transformed organisms suitable for carrying out the process of the invention also form a further aspect of the invention.

In principle, any organism may be modified to produce the desired protein in this way, for example, bacteria, yeasts, plants, or plant cells, insect cells or animal cells. Bacteria, yeasts and plants or plant cell systems are generally preferred.

It is also possible to provide suitable genetically transformed organisms, adapted to produce the AFPs of the invention, which are themselves useful on account of their increased frost resistance. In particular this applies to plants: which may be cereals such as wheat or maize; or dicotyledons such as soya, tomato or lettuce. Such plants also form part of our invention.

Anti-freeze peptides according to the invention can conveniently be used in several products, preferably in food products which are frozen or intended for freezing. Examples of such food products are: frozen food products such as vegetables, sauces, soups, snacks, dairy products and frozen confectionery, under which term we include sorbet, water-ice, granites, frozen fruit purees and milk-containing frozen confections such as ice-cream, frozen yoghurt or custards, sherbet and ice-milk. Preferred food products are frozen vegetables and frozen confectionery, e.g. ice-cream, water-ice. If dry-mixes or concentrates are used, the concentration may be higher in order to ensure that the level in the final frozen product is within the desired range. Preferred levels of AFP are from 0.00005 to 0.3%, particularly from 0.0001 to 0.2% by weight of final product.

It is not necessary to add the AFP in highly purified form: it may be added as a composition containing the AFP, for example an extract of the organism that produces the AFP.

Frozen confectionery according to the invention can be produced by any suitable method known to the art. Preferably all ingredients of the formulation are fully mixed together at or above ambient temperature before freezing. The level of solids in the frozen confection (e.g., sugar, fat, flavoring) is suitably adjusted to be at least 3% and normally in the range 10 to 70%, particularly 40 to 70%, by weight of the final product.

The invention will now be illustrated by the following non-limiting examples.

EXAMPLES

Example 1

19 Isolates were collected from various sites in Antarctic lakes. Two were found to give rise to anti-freeze proteins (see Table 1 below), isolate 196 and isolate 20. These bacteria were isolated from Ace lake and Club lake, respectively. Ace lake is meromictic: Club lake is monomictic. Both bacteria were isolated from near to the surface of the lake. Isolate 196 was isolated from the ice/water interface. Isolate 20 was isolated from the top 50 cm of water column away from the edge of the lake. More details of the two lakes are provided below:

Ace lake
  Brackish at surface—18 ppt; salinity increasing with depth to 34 ppt.
  Ice cover for 10–11 months of the year
  Meromictic—chemically and thermally stratified
Club lake
  Hypersaline (250 ppt)
  No ice cover
  Monomictic—stratified thermally in winter, water column mixed in summer Culturing of Isolates Bacterial isolates were inoculated into 200 ml of Tryptic Soya Broth (Oxoid).

Isolate 196 (*Marinomonas protea*) was also cultured in 200 ml Sea Salts Broth and 200 ml of ½ Sea Water Broth

| | | |
|---|---|---|
| Tryptic Soya Broth ["TSB"] Pancreatic digest of Caesin (Oxoid): | | 11.3 g/L |
| Papaic Digest of Soya Bean | | 2 g/L |
| Dibasic Potassium phosphate | | 1.7 g/L |
| Glucose | | 1.7 g/L |
| NaCl | | 3.3 g/L |
| pH | | 7.3 +/− 0.2 |
| Sea Salts Broth ["SSB"]: | Sea salts (Sigma) | 40 g/L |
| | Peptone (BDH) | 5 g/L |
| | Yeast Extract (Merck) | 2 g/L |
| Sea Water Broth ["SWB"]: | 'Instant Ocean' (Aquarium Systems, France) | 38 g/L |
| | Yeast Extract (Merck) | 1 g/L |
| | Peptone (BDH) | 1 g/L |
| ½ Sea Water Broth ["½SWB"]: | 'Instant Ocean' (Aquarium Systems, France) | 19 g/L |
| | Yeast Extract (Merck) | 1 g/L |
| | Peptone (BDH) | 1 g/L |

All cultures were incubated at 15° C. until noticeably turbid (this took 2–6 days depending on the growth rate of each culture). All cultures were then cold shocked at 5° C. for 4 days. 200 mls of an *E. coli* culture was also produced as a negative control. This was strain W3110. It was cultured in Lauria-Bertani ["LB"] media in a shaking vessel at 37° C. overnight.

| | | |
|---|---|---|
| LB media | Bacto-tryptone | 10 g/L |
| | Bacto-yeast extract | 5 g/L |
| | NaCl | 10 g/L |
| | Adjusted to pH 7.0 | |

Protein Extraction

The following protocol gives the method used for total cellular protein extraction.

1. The cells were collected from the cultures by centrifugation. A Beckman cooling centrifuge, with a fixed angle JA-14 rotor was used. Samples were spun at a constant temperature of 4° C. and at a speed of 10,000 rpm (15,300 g) for 10 mins. The supernatant was carefully removed leaving the pellet.

2. The pellet was resuspended in 1 ml of 10 mM Tris/HCL buffer (pH 7.0). This was repelleted using the same centrifuge conditions as step 1. The supernatant was discarded carefully leaving just the pellet.
3. The pellet was then resuspended in 1 ml of protein extraction buffer (see below) and then kept on ice for 5 mins to allow cell lysis. The resuspended pellet was then sonicated in a thick walled bottle using a Sanyo Soniprep 150 at 15 A for 30 seconds.
4. The sonicated mixture was then transferred back to a centrifuge tube and centrifuged as outlined in step 1. The supernatant was removed and frozen at −20° C. until required.

Protein Extraction Buffer:
25 mM Tris/HCL (pH-7.0)
1 mM EDTA
1 mM PMSF (Sigma)
2 ug/ml Pepstatin A (Sigma)

Splat Assay

The following protocol is the method used to view the level of ice re-crystallisation inhibition achieved by each of the protein extractions. It is a modification of the assay described in Byass et al. [Unilever WO-A-98/04148].
1. A 60% sucrose solution was prepared. A 20 µl sample of each protein extract was mixed with 20 µl of the sucrose solution. These mixtures were made up in 1.5 ml Eppendorf tubes. The 30% sucrose/protein extract solutions were spun in a MSE Micro Centaur Desk top microcentrifuge for 10 seconds to make sure all the liquid was mixed at the bottom of the tube.
2. 5 µl of the resulting solution was placed between two circular 16 mm diameter coverslips upon which the number of the extract was written in waterproof maker. These were then blotted dry.
3. The coverslips were then dropped into 2,2,4-Trimethyl pentane that had been pre-chilled to −70° C. (using dry ice). They were super-cooled in this for 2 minutes.
4. A chilled bath was filled ¾ full of 2,2,4-Trimethyl pentane, which was pre-chilled to −6° C. using a Haake C water bath circulator and two Haake temperature control units (PG40 and F4).
5. The coverslips were removed from the super-cooling process and placed directly into the −6° C. bath for 30 mins to allow re-crystallisation.
6. The coverslips were then viewed whilst in the −6° C. bath using a EF L 20/0.30 160/0-2 objective on a Leitz Dialux 20 EB stage.
7. The observed crystal shape, size and density were related to the level of AFP activity using the Splat Scoring System outlined below.

| Splat Score | Observed crystal morphologies |
| --- | --- |
| +++++ | Very small, very dense crystals. |
| ++++ | Small, not dense; or small, quite dense with some medium-sized crystals. |
| +++ | Small, not dense with medium-large crystals; or small-medium, not dense. |
| ++ | Medium or large crystals with some small crystals |
| + | Large, round discrete crystals (e.g. 30% sucrose control). |

[A score of +++ or above is required for an isolate to have any practical utility].

Results from the splat assay are shown in Table 1

TABLE 1

| Bacterial isolate activity | AFP | Bacterial isolate activity | AFP |
| --- | --- | --- | --- |
| 196 [½ SWB] | ++++ | 196 [TSB] | +++ |
| 196 [SSB] | ++++ | 18 | ++ |
| 20 | +++/++++ | 26 | + |
| 29 | +/++ | 39 | + |
| 43 | ++ | 44 | + |
| 98 | ++ | 101 | + |
| 104 | + | 118 | ++ |
| 120 | + | 125 | + |
| 184 | + | 226 | + |
| 288 | + | 121 | + |
| 289 | + | E. coli (neg. control) | + |
| Sucrose only (neg. control) | + | | |

The results in Table 1 show that out of the 19 isolates of Antarctic bacteria that were investigated, only isolate 196 isolate 20 produce proteins with significant amounts of AFP. Isolate 196 is *Marinomonas protea*, as further described below.

Example 2

Collection of Isolate 196

Bacteria were isolated from the ice/water interface of Ace Lake, Antarctica (68°28'S, 78°11'E) on 31/6/96. Samples were collected by drilling a hole through the ice (1600 mm thick) at the deepest point of the lake. Sections of the lower part of the core from the ice/water interface were melted onto agar. The material was designated Isolate 196.

Growth Characteristics of Isolate 196

Figure 2:
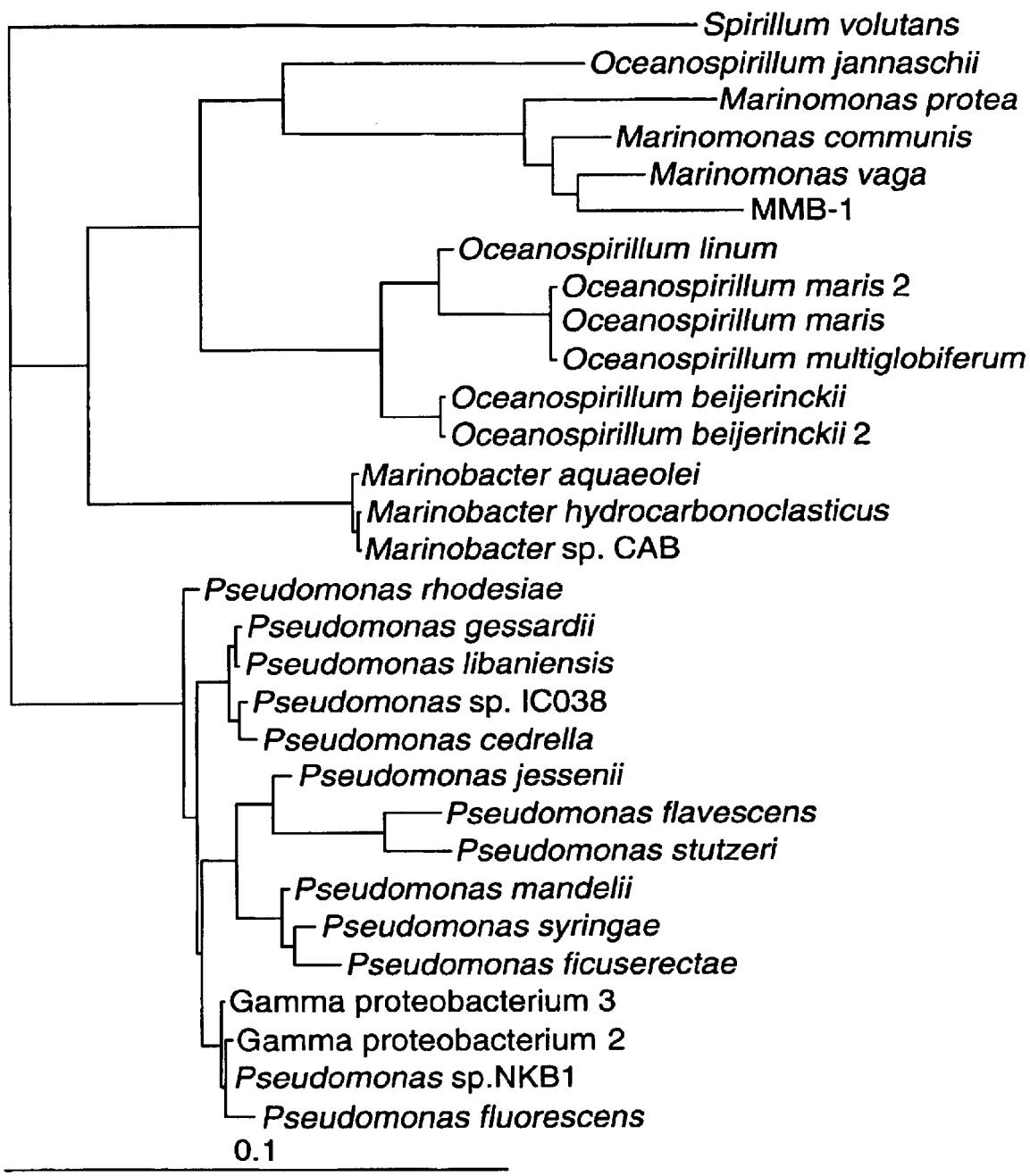
FIG. 2 is a phylogenetic tree comparing *Marinomonas protea* with its closest phylogenetic relatives.

Colonies of isolate 196 that formed on half-strength seawater agar after 3 to 5 days of incubation at 10° C. were non-pigmented (creamy colour), smooth, convex, circular with entire edges and ranged in size from less than 0.5 mm to 1.5 mm in diameter. On tryptic soya agar the colonies were beige in colour, mucoid and spreading, and ranged from 2–5 mm in diameter. The isolate was psychrotrophic, growing at temperatures between <0 to ~25° C. (optimal growth between 15–22° C.), with no growth at 30° C. The bacterium grew aerobically and under microaerophilic conditions, but would not grow anaerobically. It did not require seawater for growth, but could tolerate up to 70% NaCl. Cells growing in 60–70% NaCl consisted of straight rods and coccoid cells, which appeared more wrinkled and indented than cells in lower salinity media. Typical growth curves in different media types are shown in FIGS. 1 and 2.

Organism Classification

Analysis of 16S rRNA Phylogenetic from Isolate 196

Identification of the isolate was based on 16S rRNA analysis. A near complete (1,485-bp) sequence of the 16S rRNA gene, stretching from nucleotide positions 18 to 1503 (*Escherichia coli* equivalent numbering), was obtained and is shown in FIG. 3. 16S rRNA analyses against species in the publicly available databanks showed that it represented a novel species of the genus *Marinomonas* (in the gamma-3 subclass of the phylum Proteobacteria), with 74.7% identity to *Marinomonas communis* (the type species of the genus). The match between the two sequences is shown in FIG. 4. The name *Marinomonas protea* sp. nov. (pro'te.a. Gr. n. Proteos, name of the Greek mythological god of the sea who could appear in many shapes, M. L. fem. adj. *protea*, polymorphous) was proposed (Prof. Hans G. Trüper, *pers. comm.*). The bacterium has been deposited at the British National Collections of Industrial and Marine Bacteria, Aberdeen (NCIMB) under the number 41006 on 9, Feb. 1999.

Figure 5:
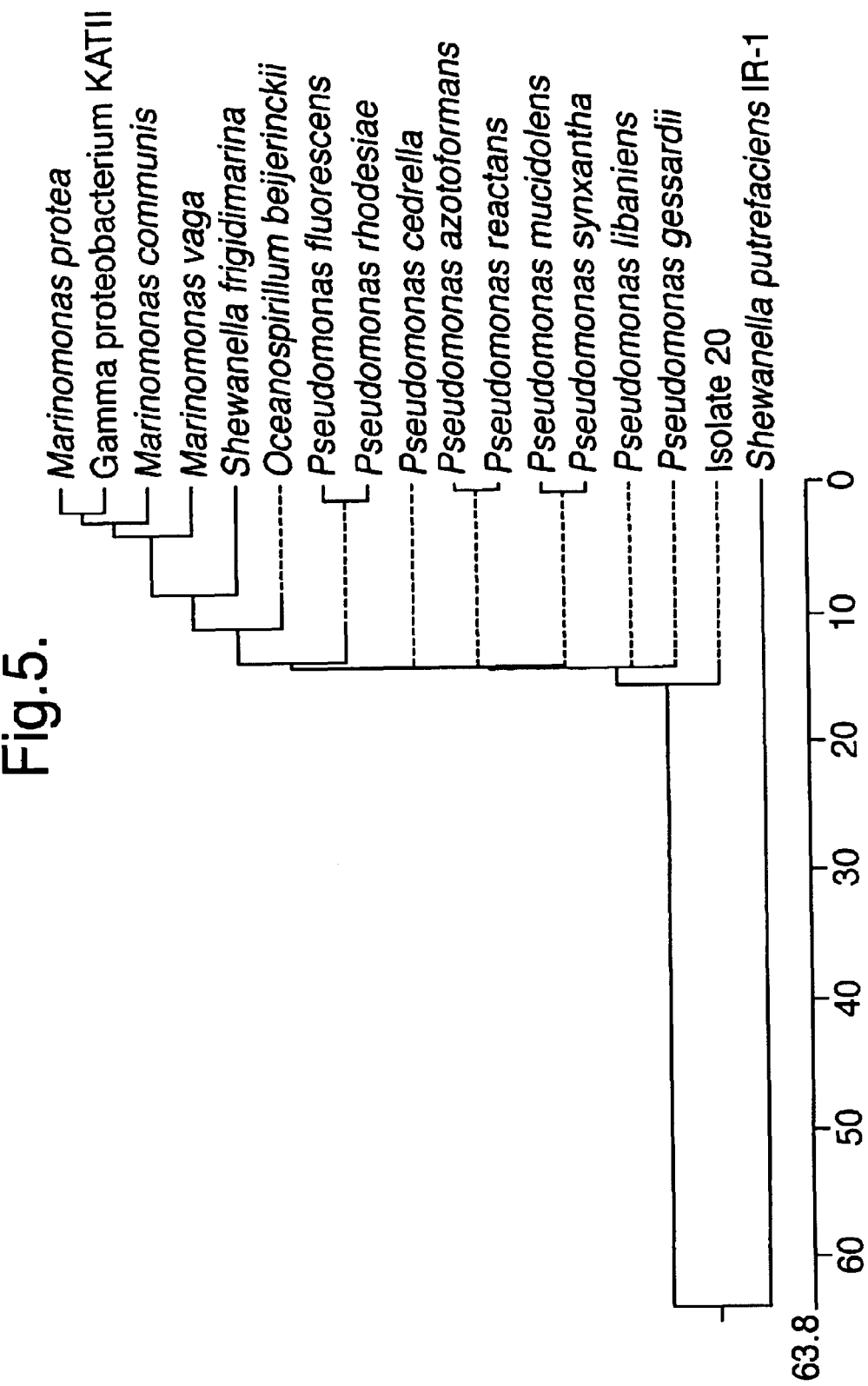
FIG. 5 is a phylogenetic tree based on 16S rRNA sequences comparing Isolate 20 (SEQ ID 2) with its closest relatives. Multiple sequence alignments were created using the Clustal method with a gap penalty of 10.

The 16S rRNA sequences generated in this study were deposited in GenBank. Percentage similarities for the sequences are given in Table I. The phylogenetic tree determined using PHYLIP (version 3.57c) is shown in FIG. 5. It uses almost complete 16S rRNA sequences, comparing *Marinomonas protea* with its closest phylogenetic relatives and with three other sea-ice isolates identified as *Marinomonas* sp. (M. Brown, *pers. comm*). The tree was constructed using the maximum likelihood method (Felsenstein, 1981).

16S rRNA Phylogenetic Analysis of Isolate 20

An analysis of Isolate 20 found it to be a species of *Pseudomonas*. More precisely, isolate 20 was found to have a similarity value of 99.4% with *Pseudomonas synxantha*. This strain was deposited under the Budapest Treaty with international depository authority NCIMB Aberdeen, Scotland under number NCIMB 41076.

Example 3

Total Cellular Protein Extraction

A bacterial culture (2 L) of Isolate 196 was grown in liquid medium (Tryptic Soy Broth) at 15° C. until turbid. The culture was aseptically pipetted into sterile Nalgene™ universals. The cells were harvested by centrifugation at 4,200×g for 12 minutes at 5° C. (Sorvall Dupont Econospin). The pellets were resuspended in 1 ml of ice-cold 10 mM Tris buffer (Tris [hydroxymethyl]amino-methane)/HCl (pH 7.0) The cells were pelleted for 10 minutes. The pellets were then either stored at −20° C. overnight, or protein extractions were carried out immediately. The pellet was resuspended in 1 ml of ice-cold native extraction buffer (NEB, which consisted of 25 mM Tris/HCl (pH 7.0), 1 mM EDTA, 1 mM PMSF and 0.1 mM Pepstatin A). The Tris buffer acts as a biochemical buffer, the EDTA is a chelating agent and is active against metalloproteases, PMSF is an inhibitor of serine proteases and Pepstatin A inhibits proteases. To each resuspended pellet, two volumes of acid-(70% HCl) washed glass beads were added (1.5 ml of 425–600 µm diameter beads and 0.5 ml of 3 mm diameter beads, both Sigma), or enough to create a viscous adherent coating of cell suspension over the beads. The beads were acid washed to prevent alkali being liberated from the glass when vortexed, as this would potentially damage alkali-sensitive components of the cells. The mixture was then vortexed for 1 minute sessions, with 1 minute intervals on ice. This was repeated 8 times for each sample, after which a further 1 ml of ice-cold NEB was added to the beads, which were re-vortexed to enable the cell suspension to go into solution. The cells were left on ice for 5 minutes to allow the glass beads to settle and the lysates were transferred to 1 ml sterile, ice-cold Eppendorf tubes and centrifuged (Beckman MSE, 12,000×g, 5° C., 5 minutes) in order to separate the cell walls and non-ruptured cells, as well as any glass beads which were accidentally transferred. The supernatant was transferred to sterile, ice-cold Eppendorfs and centrifuged once more to remove any further cell debris that may interfere with the RI assay. The supernatant was pipetted into 2 ice-cold, labelled Eppendorfs and stored at −20° C. until the assays were carried out.

Example 4

Effect of Bacterial Anti-freeze Proteins on Ice Crystal Morphology

The effect of the anti-freeze protein from isolate 196 (obtained as in Example 3) on ice crystal morphology was assessed by examining total cellular protein extract at −6° C. under the microscope. Hexagonal ice crystals, some elongated, were clearly visible.

Example 5

Protein Purification and Sequence Information Purification of Active Protein

The bacterial anti-freeze protein, which we term marinomonin, was isolated from the crude extract produced in Example 3 using reverse phase chromatography (RPC) on an AKTA™ protein purification system, followed by gel exclusion chromatography (Sephadex® 75, or S75) on a SMART™ system (both Pharmacia Biotech). The active fractions from each separation method were run on a 10% bis-acrylamide SDS gel: the band obtained ran at a molecular weight of ~38 kDa.

Sequence Information

The 38 kDa protein band was electroblotted onto a PVDF membrane and N-terminal sequenced. The following sequence of 16 amino acids was obtained, with the 6th amino acid producing an ambiguous result of either Glycine or Valine (shaded region indicates region of sequence that the oligonucleotide probe was designed from):

(Seq ID 3)
Ala-Glu-Gly-Ser-Thr-Gly/Val-Asp-Val-Tyr-Gln-
Asn-Ile-Gln-Tyr-Ala-Gly

Database Homology Searches

Sequence homology searches were carried out using the N-terminal sequence of the novel AFP protein using FASTA searches against the SWISS-PROT database, which included all published AFP sequences. The sequence matches were random, in that similarities were matched to a wide range of organisms, both bacterial and eukaryotic, and the similarities were not particularly high. Also, the regions of homology between the protein sequences were not located at the N-terminus of the proteins on the database, but mid-sequence: this reduces the likelihood of any real homology between the protein sequences and the N-terminal sequence of this novel protein.

Example 6

Two important requirements for an AFP-producing micro-organism to be of practical utility is that its culturing can be readily scaled-up and that the AFP-activity is stable. For example, susceptibility to denaturation by heat makes it more difficult to use the AFP in foodstuffs such as ice cream that are pasteurized during manufacture.

Culturing *Marinomonas protea* in "shake flasks" (9 liters scale)

Isolate 196 (*Marinomonas protea*) was cultured in 18 individual 1 L Erlenmeyer flasks containing 500 ml of sterile Sea Salts Broth (sea salts (Sigma) 40 g/L; peptone (Fisher) 5 g/L; yeast extract (Difco) 2 g/L). Flasks were inoculated aseptically with 100 µl of an existing *M. protea* culture. Cultures were grown statically at 15° C. for 7 days in a Sanyo incubator. The cultures showed signs of turbidity following 2 days at 15° C. On day 7 the incubator temperature was adjusted to 4° C. and maintained at this temperature for a further 7 days to induce anti-freeze protein (AFP) production.

Following 7 days cold induction at 4° C., cells from the 9 L, of culture were collected in 6 sterile 300 ml containers by repeated centrifugation. Centrifugation was carried out at 7000 rpm for 20 minutes and at 4° C. using a Sorvall F-16/250 fixed angle rotor in a Sorvall Instruments RC5C centrifuge. Following each centrifugation step the supernatant was discarded and further culture added and centrifugation repeated. In this way, pellets were accumulated in the 6 containers until the 9 L of culture was harvested. The six containers and associated pellets were stored at −80° C. until required for protein extraction and SPLAT testing.

Protein Extraction from 9 Liter Culture and Splat Testing for AFP Activity

Pellets were washed by gentle resuspension in 10 ml of ice cold 10 mM Tris/HCl (pH 7.0). A 1 ml aliquot of the resuspended cells was centrifuged in an Eppendorf tube for 5 minutes at 13,000 rpm in a microcentrifuge (MSE Micro Centaur). The 'wash supernatant' was retained for testing for AFP activity by the SPLAT assay. The pelleted cells (~0.2 g) was resuspended in 800 µl of ice cold extraction buffer (50 mM Tris/HCl, pH 7.0) and 200 µl of Bacterial protease inhibitor cocktail supplied by Sigma. [This cocktail contains a mixture of protease inhibitors with broad specificity for the inhibition of serine, cysteine, aspartic and metallo-proteases, and aminopeptidases. It comprises 4-(2-aminoethyl) benzenesulfonyl fluoride (AEBSF), pepstatin-A, trans-epoxysuccinyl-L-leucyl-amido(4-guanidino) butane (E-64), bestatin, and sodium EDTA]. The samples were vortexed and then placed in ice, and this process was repeated a total of 8 times. The samples were then centrifuged and the 'extraction supernatant' retained for AFP testing by the SPLAT assay.

| SPLAT activity | |
|---|---|
| Material | SPLAT score |
| 'Wash supernatant' | ++++ |
| 'Extraction supernatant' | +++ |

Example 7

Induction of AFP by Cold-shocking a Culture at 8° C.

For the AFP production to be readily scaled-up, it is important that cold-shocking can be effective at a range of different temperatures. For example, it is difficult to operate fermenters at temperatures below 8° C. Therefore, to be able to scale-up production in fermenters, it must be possible to induce expression of AFP by cold-shocking at temperatures of 8° C. or above. This example shows that *Marinomonas protea* cultures can be induced to express AFP at 8° C.

Isolate 196 (*Marinomonas protea*) was cultured in a 1 L Erlenmeyer flask containing 500 ml of sterile Sea Salts Broth (sea salts (Sigma) 40 g/L; peptone (Fisher) 5 g/L; yeast extract (Difco) 2 g/L). The flask was inoculated aseptically with 100 µl of an existing *M. protea* culture. The culture was grown statically at 15° C. for 7 days in a Sanyo incubator. The culture showed signs of turbidity following 2 days at 15° C. On day 7, the culture was transferred to a Conviron incubator set to 8° C. and this temperature was maintained for a further 7 days to induce anti-freeze protein (AFP) production.

Following 7 days cold induction at 8° C., the *M. protea* culture was harvested and tested for AFP activity by the SPLAT assay. The 500 ml of culture was collected in a 50 ml container by repeated centrifugation. Centrifugation was carried out at 9000 rpm for 5 minutes at 4° C. using a Sorvall SS34 rotor in a Sorvall Instrument RC5C centrifuge. Following each centrifugation step, the supernatant was discarded and further culture added and centrifugation repeated. In this way a pellet accumulated in the container until the 500 ml of culture was harvested. The resulting cell pellet weighed 0.9 g.

The 0.9 g of pelleted cells were gently resuspended in 1 ml of ice cold extraction buffer (25 mM Tris/HCl, pH 7.0) and 0.5 ml of Bacterial protease inhibitor cocktail supplied by Sigma (see Example 6). The sample was vortexed and then placed on ice, and this process was repeated a total of 8 times. The sample was then centrifuged for 10 minutes at 18000 rpm using a Sorvall SS34 rotor in a Sorvall Instrument RC5C centrifuge and the 'extraction supernatant' was filtered using a 0.2 µm filter and retained for SPLAT activity determination (see table).

| Material | SPLAT score |
|---|---|
| 'Extraction supernatant' | ++++(+) |

Example 8

Heat Stability of AFP Extracted from *Marinomonas protea*

An AFP-containing extract was prepared from a culture of *Marinomonas protea*, essentially as described in Example 6. 25 µl aliquots (5 in total) were placed in 500 µl Eppendorf tubes and tested for heat stability. Four of the tubes were placed in a bath of boiling water. Each tube was exposed to the heat treatment for a different length of time: either 1, 2, 5, or 15 minutes. The fifth tube was used as a control and was not exposed to the heat treatment. After the heat treatment, all tubes were immediately placed on ice and then assayed for AFP activity using the splat assay.

| SPLAT activity following boiling | |
|---|---|
| Treatment | SPLAT score |
| *Marinomonas protea* extract, not boiled | +++++ |
| *Marinomonas protea* extract, boiled 1 min | +++++ |
| *Marinomonas protea* extract, boiled 2 min | +++++ |
| *Marinomonas protea* extract, boiled 5 min | +++++ |
| *Marinomonas protea* extract, boiled 15 min | ++++ |

As the AFP extracted from *Marinomonas protea* can survive boiling it is suitable for use in food-stuffs that are pasteurised during their manufacture. For example, an ice-cream "mix" would typically be pasteurised by holding at a temperature of 82° C. for 25 seconds before cooling and freezing. This example shows that the AFP extracted from *Marinomonas protea* could undergo such a pasteurisation process without loss of AFP activity.

Example 9

A preferred process is described below for isolation of AFP from *Marinomonas protea*.

a) Culturing Cells 10 litres of culture were produced as previously described in example 6 (growth at 15° C. and induction at 4° C.). Cells were harvested by centrifugation and kept at −80° C. until required.

b) Protein Extraction

Cells were resuspended in extraction buffer (20 mM tris, 10 mM EDTA, pH 7.1) and then sonicated 10 times for 15 seconds at 45 second intervals using a Sanyo Soniprep150 probe at Amplitude 12$\mu$. The extracts were placed in an ice/ethanol bath during the sonication procedure to avoid overheating the extracts.

c) Heat Treatment to Inactivate Proteases

The extract was placed in a boiling water bath for 4.5 minutes. The temperature of the samples was measured and found to reach 73° C. We have found that this is a very effective way of inactivating the proteases in the sample, and at the same time killing most or all of the bacteria (*Marinomonas protea*) in the sample.

d) Separation of AFP from Cell Debris

Extracts were centrifuged for 1 hour at 4° C. at 16,000 rpm in a Sorval Centrifuge (SS-34 rotor) to remove cell debris. AFP was found to be present in the supernatant.

e) Removal of Remaining Viable Bacteria

For many frozen foods, such as ice cream, it is important to ensure the removal of all viable bacteria. This ensures that products and equipment can be maintained to high standards of hygiene. For AFP preparations in the invention, we have found that this can be achieved by microfiltration. In this example, the supernatant described above in (d) was filtered with a Nalgene 0.2 $\mu$m sterilisation unit. The filtrate was collected in sterile tubes and stored at -80° C. until required.

f) Quality Assurance—Measurement of AFP Activity and Viable Cells Throughout the Process At each step of the process, the extracts were assayed with the splat assay. The extracts were also tested for the presence of bacterial cells. Petri dishes containing Trypton Soya agar from Sigma were used (40 g diluted in 1L). Samples were streaked with a loop on a Petri dish or plated with a spreader (50 $\mu$l) and incubated for 7 days at 15° C.

The samples were

N1: Cells resuspended in Extraction buffer (Splat score ++++).

N2: Cells in Extraction buffer and after sonication (Splat score +++++).

N3: Cells in Extraction Buffer, after sonication and boiling for 4 min30 sec (Splat score +++++).

N4: N3 centrifuged for 1 hour and filtered on 0.2 $\mu$ sterilisation unit (Splat score +++++).

| Sample number | N1 | N2 | N3 | N4 |
|---|---|---|---|---|
| 3 days incubation Loop | ✓ | ✓ | X | X |
| 3 days incubation 50 ul | ✓ | ✓ | X | X |
| 7 days incubation Loop | ✓✓ | ✓✓ | X | X |
| 7 days incubation 50 ul | ✓✓ | ✓✓ | 1 colony contaminant | X |

✓ Presence of colonies in the Petri Dish
X Absence of colonies

Conclusion

AFP produced by this process is: a) active, b) free from viable cells, and c) free from toxic chemicals.

Example 10

In this example it is demonstrated how to determine how much AFP-containing solution to add to the food-stuff by using the "Re-crystallisation Inhibition (RI) assay". The RI assay is quantitative but it is also time-consuming and requires special equipment. An assay for measuring ice re-crystallisation inhibition has previously been described by Jarman et al. (WO 99/37782). In this example, the protocol given below was used.

RI Assay Protocol

A solution containing AFP from *Marinomonas protea* was adjusted to a sucrose level of 30 wt % with sucrose crystals. A 3 $\mu$l drop of the sample was placed on a 22 mm coverslip. A 16 mm diameter cover-slip was then placed on top and a 200 g weight was placed on the sample to ensure a uniform slide thickness. The edges of the coverslip were sealed with clear nail varnish. The slide was placed on a Linkam THM 600 temperature controlled microscope stage. The stage was cooled rapidly (50° C. per minute) to -40° C. to produce a large population of small crystals. The stage temperature was then raised rapidly (50° C. per minute) to -6.0° C. and held at this temperature. The ice-phase was observed at -6.0° C. using a Leitz Ortholux II microscope. Polarised light conditions in conjunction with a lambda plate were used to enhance the contrast of the ice crystals. Images were recorded at T=0 and T=60 minutes and analysed using image analysis software (AnalySIS, Soft-Imaging Software GmbH, D48153, Munster, Hammerstrasse, 89 Germany). The crystal growth was calculated as follows.

The mean size of a population of ice crystals at a particular time was determined by capturing an image of the population (using the equipment mentioned above) and then selecting a region of the image that contained at least 200 ice crystals. The longest diameter of each crystal was determined by drawing around them and calculating the longest diameter using the image analysis software.

Each RI experiment was carried out 3 times (therefore the images of at least 600 ice crystals were analysed). The data in the table record the mean ice crystal growth (i.e. the difference in the mean ice crystal diameter at time zero and after 60 minutes). Confidence limits were calculated for a confidence level in the mean of 95%.

Several dilutions of a preparation of *Marinomonas* AFP were made in order to find out how far the sample could be diluted and still achieve an effective inhibition of re-crystallisation of ice. In practical terms we consider an AFP preparation or a dilution of an AFP preparation to achieve an effective inhibition of re-crystallisation of ice if a sample of said dilution or preparation results in ice crystal growth in the RI assay of 3 $\mu$m or less.

RI Assay Results

Mean crystal growth was determined by analyzing the images of 1200 crystals.

Figure 6A:
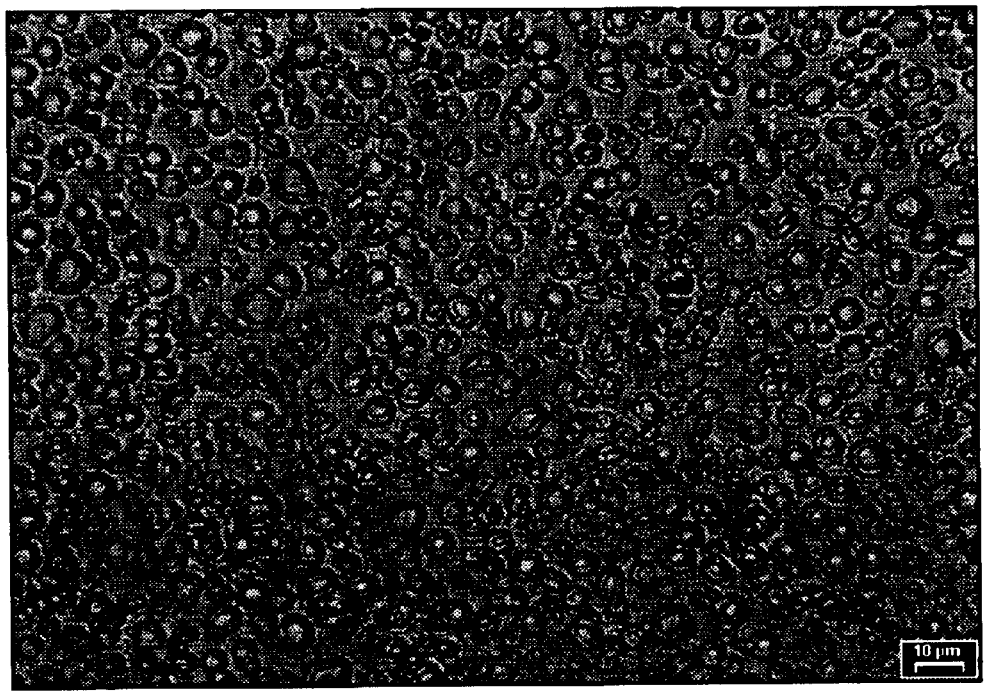
FIG. 6 shows the result of an RI experiment at time=0 (6A) and at time=60 minutes (6B).
Figure 6B:
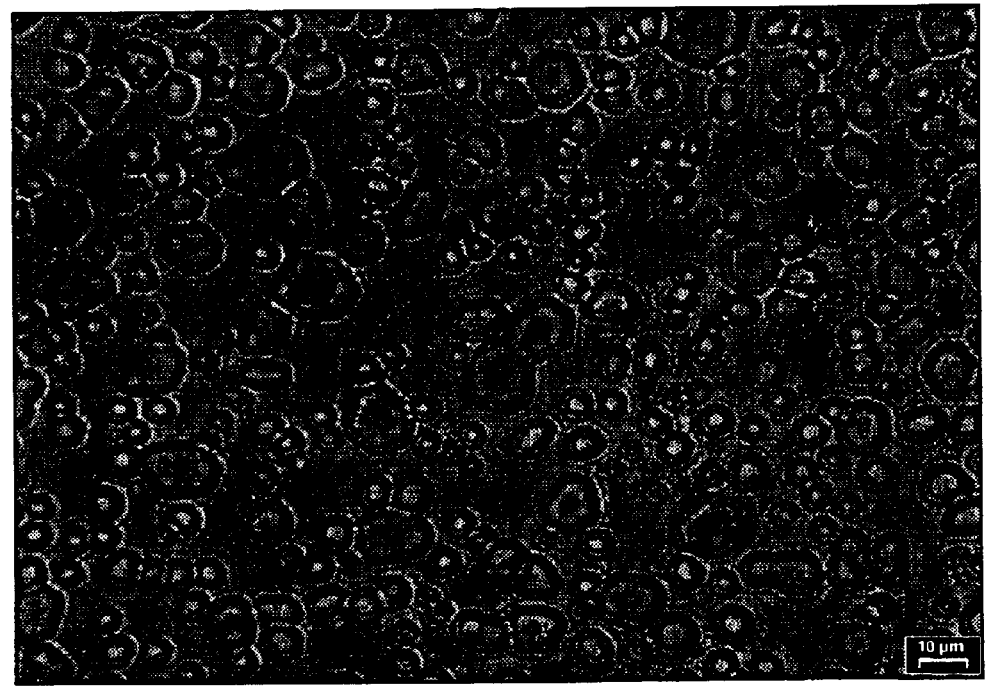

FIGS. 6A and 6B illustrate typical ice crystal images simply to show the type of image that was captured and analysed.

| Dilution of AFP preparation | Crystal growth (mean in $\mu$m) | Confidence limits |
|---|---|---|
| 1 in 10 | 1.96 | +/-0.64 |
| 1 in 20 | 3.72 | +/-0.79 |
| 1 in 100 | 9.87 | +/-2.04 |
| Negative control (no AFP) | 12.78 | +/-1.61 |

The results show that the AFP preparation can be diluted 10-fold and still an effective inhibition of the re-crystallisation of ice is achieved. Therefore, a 1 in 10 dilution (=10%) of this preparation was used in frozen food prototypes as shown in example 11.

Example 11
Preparation of Water Ice Samples

Three liquid pre-mixes were made for the preparation of water-ice:

- A) 20% sucrose in water (negative control; not according to the invention)
- B) 20% sucrose in water containing AFP from *Marinomonas*. The AFP had been diluted in the pre-mix to a concentration that would give an RI value of approximately 1.9 μm. In this instance this was a dilution of 1 in 10 or 10%—see example 10 for RI data.

Therefore, pre-mix B had the following composition:

| Ingredient | % by weight |
|---|---|
| Sucrose | 20.00 |
| AFP preparation (in aqueous buffer) | 10.00 |
| Water | 70.00 |

C) 20% sucrose in water containing fish AFP type III, HPLC 12 as described in WO-A-97/02343. The AFP had been diluted in the pre-mix to a concentration that would give an RI value of approximately 2.9 μm.

Determination of Hardness

Cuboid bars of water ice (10 mm×55 mm×95 mm) were prepared for each composition (A, B, C) as follows. Each composition, was frozen to −3.5° C. in a Gelato Chef 2000 (Magimix UK Ltd) Ice Cream maker. The mixture was transferred to silicone rubber moulds with internal dimensions of 10 mm×55 mm×95 mm, previously cooled to −30° C. The preparation was then cooled at −30° C. for 1 hour before de-moulding and storing at −25° C. prior to hardness testing, using the Vickers Hardness test.

The Vickers Hardness Test

The Vickers Hardness test is an indentation test that involves pushing a pyramid shaped indentor into the surface of material and recording the force applied as a function of tip displacement. Force and displacement are measured during the indentation loading cycle and the unloading cycle. The test is described in "Handbook of Plastics Test materials" Ed. R. P. Brown, Pub. George Godwin Limited, The Builder Group, 1–3 Pemberton Row, Fleet Street, London, 1981. The Vickers pyramid geometry is an engineering industry standard (BSi 427, 1990). It has an apex angle at the tip of 136°. Hardness is determined as:

$$H_V = \frac{F_{max}}{A}$$

where $H_v$ is the Vickers Hardness, $F_{max}$ is the maximum applied force (see FIG. 7) and A is the projected area of the indentation left in the material's surface. The area A is determined by assuming the indentation has the same geometry as the indentor that formed it, i.e. a Vickers pyramid, and therefore the projected area can be determined from the indent depth given by di in FIG. 8.

$$A = 24.5 d_1^2$$

Determination of Strength and Modulus

Several (10 or more) thin strips of water ice (50 mm×10 mm×2 mm) were prepared for each composition (A, B, C) as follows. A silicone rubber mould was accurately cut to give internal dimensions of 50 mm×10 mm×2 mm. The mould was placed on a sheet of acetate and pressed firmly to give a water tight seal. Each composition was pipetted into one such mould using a high precision micropipette, and any air bubbles were removed. A second sheet of acetate was unrolled over the top of the full mould and again any air bubbles were removed. The composition was frozen by placing the whole assembly between two nitrogen-cooled blocks at −30° C. for 2 minutes. After this time, the mould was removed and equilibrated at −20° C. The strips were demoulded by removing the upper sheet of acetate, followed by the silicone rubber mould before the basesheet was inverted and peeled back to reveal the strip of water ice. These strips were stored at −25° C. prior to testing for strength and modulus, using a three point bend test.

Three-Point Bend Test

Figure 8:
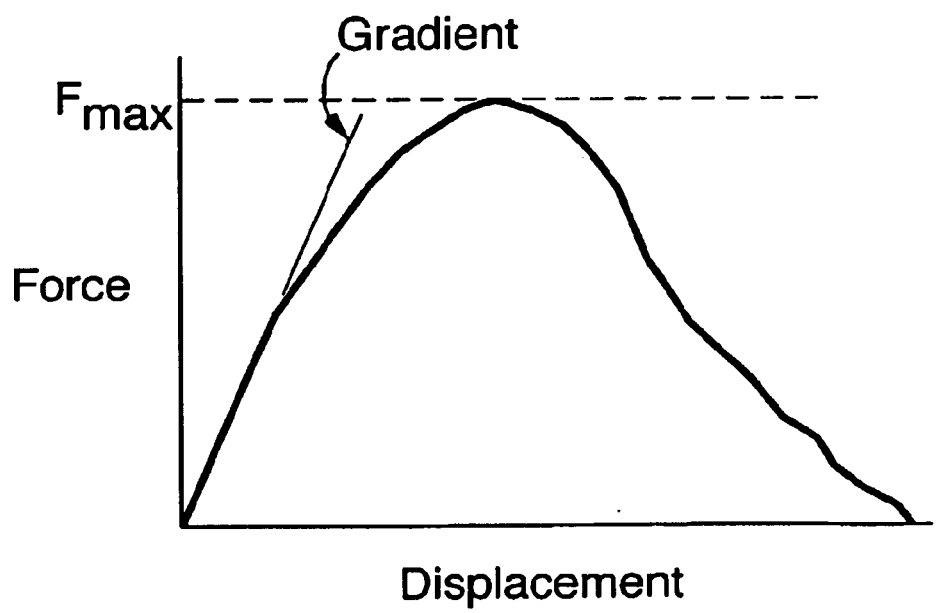
Figure 9:
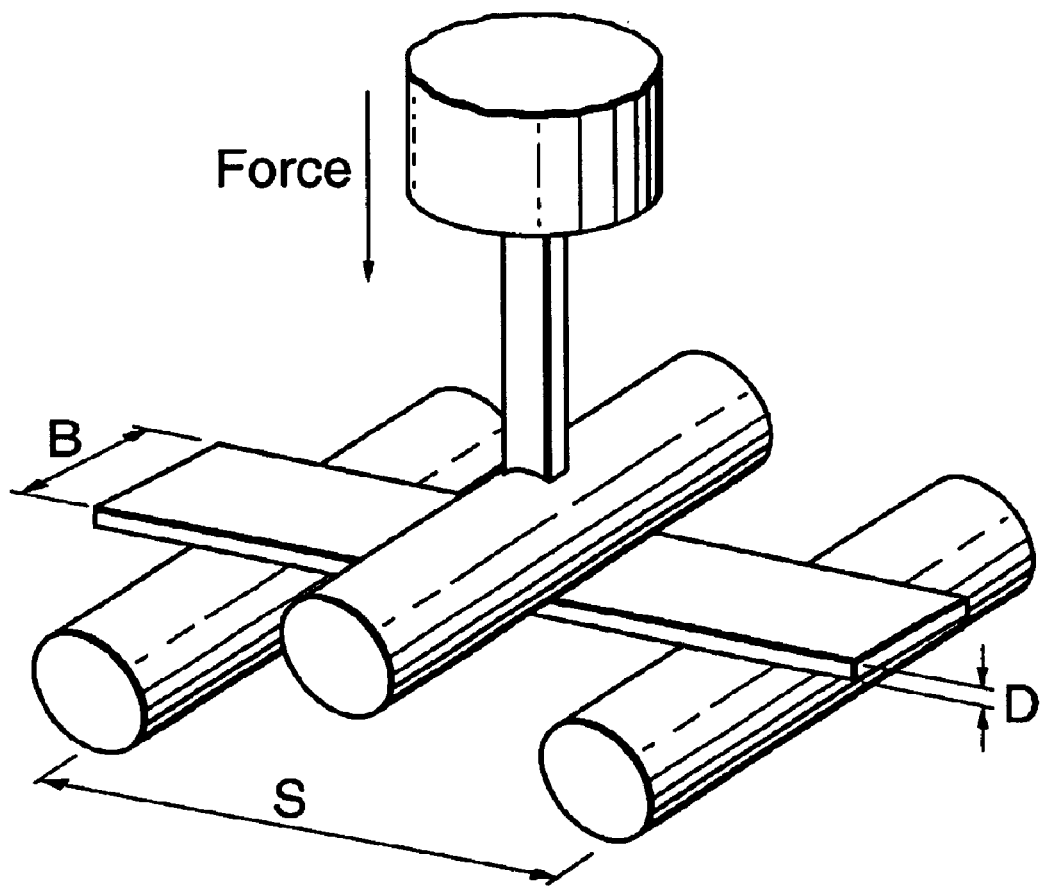

A bend test can be used to determine a number of mechanical properties of ice confection materials, such as Young's modulus (apparent) and flexure strength. In a bend test, a test piece is deformed whilst measuring the applied force and test piece deflection. A schematic data set for an ice confection is shown in FIG. 8. The elastic modulus is determined by the gradient of the initial linear part of this curve. The general test applied to all types of solids is described in "Biomechanics Materials. A practical Approach" Ed. J. F. V. Vincent, Pub. IRL Press, Oxford University Press, Walton Street, Oxford, 1992 and "Handbook of Plastics Test materials" Ed. R. P. Brown, Pub. George Godwin Limited, The Builder Group, 1–3 Pemberton Row, Fleet Street, London, 1981. In this particular application, a 3-point bend test was adapted to evaluate thin strips of water ice (50 mm×10 mm×2 mm; prepared as above) whilst in a temperature controlled cabinet set at −20° C. Testing involved placing each strip onto 2 supports separated by 30 mm and applying pressure from an upper support centrally onto the strip's surface (FIG. 9). The force applied in bending and the displacement of the moving contact were recorded throughout the test. The speed of descent of the moving support was 10 mm per minute.

The apparent elastic modulus of the material is given by the equation;

$$E = \frac{\text{gradient} \cdot S^3}{4BD^3}$$

where the gradient is that shown in FIG. 8, S is the span (distance) between the supporting contacts beneath the test strip, B is the width of the strip and D is the depth of the strip For these tests the span (S) was 30 mm. With reference to FIG. 8, the strength of a material under three point bend conditions, is given as;

$$\sigma_u = \frac{3 \cdot F_{max} S}{2BD^2}$$

where $\sigma_u$ is the flexure strength and $F_{max}$ is the maximum force recorded.

Results of Mechanical Property Testing

Results for the 3 different water ice compositions are given below. Data were recorded as the mean, as derived from making 10 measurements. In the case of hardness testing, 10 measurements were made on one water ice bar (10 mm×55 mm×95 mm). In the case of strength and modulus, one measurement was made on each of 10 individual water ice strips (50 mm×10 mm×2 mm).

| Sample | Hardness (MPa) | Strength (MPa) | Modulus (MPa) |
|---|---|---|---|
| A - Negative control (no AFP) | 13.64 | 1.12 | 413 |
| B - Contains Marinomonas AFP | 9.00 | 0.61 | 248 |
| C - Contains fish AFP type III hplc12 | 19.34 | 2.20 | 1033 |

Surprisingly, the results show that the samples containing *Marinomonas* AFP were not hard or brittle, despite the fact that the fish AFP and *Marinomonas* AFP were each added in similar levels in terms of their RI-activity.

What is claimed is:

1. An isolated protein having anti-freeze activity and having an N-terminal amino acid sequence as set forth in SEQ ID NO: 3.

2. A food product comprising a protein according to claim 1.

3. The food product according to claim 2 wherein the food product is selected from the group comprising frozen vegetables and frozen confectionery.

4. The food product according to claim 3 wherein the food product is ice cream.

5. An isolated protein having anti-freeze activity which protein is isolated from a pure bacterial culture of *Marinomonas* species that generate anti-freeze proteins, said *Marinomonas* species comprising a 16S rRNA gene having at least 95% identity with the corresponding sequence from the organism *Marinomonas protea* deposited under Accession No. NCIMB 41006.

6. An isolated protein having anti-freeze activity which protein is isolated from a pure bacterial culture of *Pseudomonas* species deposited under Accession No. NCIMB 41076.

7. The isolated protein of claim 5 wherein the *Marinomas* species is the organism *Marinomonas protea* deposited under Accession No. NCIMB 41006.

8. A food product comprising a protein according to claim 5.

* * * * *

SEQUENCE LISTING

<160> NUMBER OF SEQ ID NOS: 5

<210> SEQ ID NO 1
<211> LENGTH: 1486
<212> TYPE: DNA
<213> ORGANISM: Marinomonas protea

<400> SEQUENCE: 1

```
gttagctcag attgaacgct ggcggcaggc ttaaacacat gcaagtcgag cggtaacagg      60
ggagcttgct cctgctgacg agcggcggac gggtgagtaa cgcgtaggaa tctgcctagt     120
agaggggac  aacatgtgga aacgcatgct aataccgcat acgccctgag ggggaaagga     180
ggggactctt cggagccttc cgctattaga tgagcctgcg tgagattagc tagttggtag     240
ggtaaaggcc taccaaggcg acgatctcta actggtctga gaggatgacc agtcacactg     300
ggactgagac acggcccaga ctcctacggg aggcagcagt ggggaatatt ggacaatggg     360
cgcaagcctg atccagccat gccgcgtgtg tgaagaaggc cttaggguttg taaagcactt     420
tcagggtga  ggaagggtga taggttaata cgttatcatc ttgacgttag ccccagaaga     480
agcaccggct aactctgtgc cagcagccgc ggtaatacag agggtgcaag cgttaatcgg     540
aattactggg cgtaaagcgc gcgtaggtgg tttgttaagt cggatgtgaa atcccagggc     600
tcaaccttgg aatggcaccc gatactggct agctagagta tggtagaggg gtgtggaatt     660
tcctgtgtag cggtgaaatg cgtagatata ggaaggaaca tcagtggcga aggcgacacc     720
ctggactaat actgacactg aggtgcgaaa gcgtggggag caaacaggat tagataccct     780
ggtagtccac gccgtaaacg atgtctacta gccgttgggt tgtaatgact agtggcgca      840
gctaacgcaa taagtagacc gcctgggag  tacggccgca aggttaaaac tcaaatgaat     900
tgacggggggc ccgcacaagc ggtggagcat gtggtttaat tcgaagcaac gcgaagaacc     960
ttacctactc ttgacatcca cagaacattt gagagatcag atggtgcctt cgggaactgt    1020
gagacaggtg ctgcatggct gtcgtcagct cgtgttgtga aatgttgggt taagtcccgt    1080
aacgagcgca accttgtcc  ttatttgcca gcacgtaatg gtgggaactt taaggagact    1140
gccggtgaca aaccggagga aggtgggac  gacgtcaagt catcatggcc cttacgagta    1200
gggctacaca cgtgctacaa tggcgtatac agagggctgc aagctagcga tagtgagcga    1260
atcccacaaa gtacgtcgta gtccggattg gagtctgcaa ctcgactcca tgaagtcgga    1320
atcgctagta atcgtgaatc agaatgtcac ggtgaatacg ttcccgggcc ttgtacacac    1380
cgcccgtcac accatgggag ttgattgctc cagaagtagc tagcttaacc cttcggggat    1440
ggcggttacc acggagtggt caatgactgg ggttgaagtc tacgcg                   1486
```

<210> SEQ ID NO 2
<211> LENGTH: 1070
<212> TYPE: DNA
<213> ORGANISM: Pseudomonas (NCIMB 41076)

<400> SEQUENCE: 2

```
gcccttgctc agattgaacg ctggcggcag gcctaacaca tgcaagtcga gcggtagaga      60
gaagcttgct tctcttgaga gcggcggacg ggtgagtaat gcctaggaat ctgcctggta     120
gtgggggata cgttcggaa acggacgcta ataccgcata cgtcctacgg gagaaagcag     180
gggaccttcg ggccttgcgc tatcagatga gcctaggtcg gattagctag ttggtgaggt     240
aatggctcac caaggcgacg atccgtaact ggtctgagag gatgatcagt cacactggaa     300
ctgagacacg gtccagactc ctacgggagg cagcagtggg gaatattgga caatgggcga     360
aagcctgatc cagccatgcc gcgtgtgtga agaaggtctt cggattgtaa agcactttaa     420
gttgggagga agggttgtag attaatactc tgcaattttg acgttaccga cagaataagc     480
accggctaac tctgtgccag cagccgcggt aatacagagg gtgcaagcgt taatcggaat     540
tactgggcgt aaagcgcgcg taggtggttt gttaagttgg atgtgaaatc cccgggctca     600
acctgggaac tgcattcaaa actgactgac tagagtatgg tagagggtgg tggaatttcc     660
tgtgtagcgg tgaaatgcgt agatatagga aggaacacca gtggcgaagg cgaccacctg     720
gactaatact gacactgagg tgcgaaagcg tggggagcaa acaggattag ataccctggt     780
agtccacgcc gtaaacgatg tcaactagcc gttggaagcc ttgagctttt agtggcgcag     840
ctaacgcatt aagttgaccg cctggggagt acggccgcaa ggttaaaact caaatgaatt     900
gacgggggcc cgcacaagcg gtggagcatg tggtttaatt cgaagcaacg cgaagaacct     960
taccaggcct tgacatccaa tgaactttct agagatagat tggtgccttc gggaacattg    1020
agacaggtgc tgcatggctg tcgtcagctc gtgttgtgaa atgtaagggc                1070
```

<210> SEQ ID NO 3
<211> LENGTH: 16
<212> TYPE: PRT
<213> ORGANISM: Marinomonas protea
<220> FEATURE:
<221> NAME/KEY: VARIANT
<222> LOCATION: (6)..(6)
<223> OTHER INFORMATION: residue 6 is G or V

<400> SEQUENCE: 3

```
Ala Glu Gly Ser Thr Xaa Asp Val Tyr Gln Asn Ile Gln Tyr Ala Gly
1               5                   10                  15
```

<210> SEQ ID NO 4
<211> LENGTH: 1481
<212> TYPE: DNA
<213> ORGANISM: Marinomonas communis
<220> FEATURE:
<221> NAME/KEY: Unsure
<222> LOCATION: (1)..(1)
<223> OTHER INFORMATION: base identity unsure
<221> NAME/KEY: Unsure
<222> LOCATION: (203)..(204)
<223> OTHER INFORMATION: base identity unsure
<221> NAME/KEY: Unsure
<222> LOCATION: (840)..(840)
<223> OTHER INFORMATION: base identity unsure
<221> NAME/KEY: Unsure
<222> LOCATION: (964)..(965)
<223> OTHER INFORMATION: base identity unsure
<221> NAME/KEY: Unsure
<222> LOCATION: (1142)..(1142)
<223> OTHER INFORMATION: base identity unsure

```
<221> NAME/KEY: Unsure
<222> LOCATION: (1182)..(1182)
<223> OTHER INFORMATION: base identity unsure
<221> NAME/KEY: Unsure
<222> LOCATION: (1185)..(1186)
<223> OTHER INFORMATION: base identity unsure
<221> NAME/KEY: Unsure
<222> LOCATION: (1449)..(1449)
<223> OTHER INFORMATION: base identity unsure

<400> SEQUENCE: 4
naaactgaag agtttgatca tggctcagat tgaacgctgg cggcaggctt aacacatgca        60
agtcgagcgg taacattgct agcttgctag aagatgacga gcggcggacg ggtgagtaac       120
gcgtaggaat ctgcctagta gtgggggaca acatgtggaa acgcatgcta ataccgcata       180
cgccctacgg gggaaaggag ggnntcttcg dacctttcgc tattagatga gcctgcgtga       240
gattagctag ttggtggggt aaaggcctac caaggcgacg atctctagct ggtctgagag       300
gatgatcagc cacactggga ctgagacacg gcccagactc ctacgggagg cagcagtggg       360
gaatattgga caatgggcgc aagcctgatc cagccatgcc gcgtgtgtga agaaggcctt       420
agggttgtaa agcactttca ggagtgagga agggcgtata gttaatacct gtatgttttg       480
acgttaactc cagaagaagc accggctaac tctgtgccag cagccgcggt aatacagagg       540
gtgcgagcgt taatcggaat tactgggcgt aaagcgcgcg taggcggttt gttaagtcgg       600
atgtgaaatc ccagggctca accttggaat ggcacccgat actggcaggc tagagtacgg       660
tagaggggtg tggaatttcc tgtgtagcgg tgaaatgcgt agatatagga aggaacatca       720
gtggcgaagg cgacaccctg gaccgatact gacgctgagg tgcgaaagcg tggggagcaa       780
acaggattag ataccctggt agtccacgcc gtaaacgatg tctactagcc gttggggatn       840
tatttcttta gtggcgcagc taacgcgata agtagaccgc ctggggagta cggccgcaag       900
gttaaaactc aaatgaattg acgggggccc gcacaagcgg tggagcatgt ggtttaattc       960
gaannaacgc gaagaacctt acctactctt gacatccaga gaactttyca gagatgaatt      1020
ggtgccttcg ggaactctga dacaggtgct gcatggctgt cgtcagctcg tgttgtgaaa      1080
tgttgggtta agtcccgtaa cgagcgcaac ccttatcctt atttgccagc acttcgggtg      1140
gnaactctaa ggagactgcc ggtgacaaac cggaggaagg tnggnncgac gtcaagtcat      1200
catgccctt acgagtaggg ctacacacgt gctacaatgg cgtatacaga gggcagcgaa      1260
ctcgcgaggg taagcaaatc ccaaaaagta cgtcgtagtc cggattggag tctgcaactc      1320
gactccatga agtcggaatc gctagtaatc gtgaatcaga atgtcacggt gaatacgttc      1380
ccgggccttg tacacaccgc ccgtcacacc atgggagttg attgctccag aagtagctag      1440
cttaacctnc gggatggcgg ttaccacgga gtggtcaatg a                          1481

<210> SEQ ID NO 5
<211> LENGTH: 1140
<212> TYPE: DNA
<213> ORGANISM: Pseudomonas synxantha

<400> SEQUENCE: 5
agagtttgat cttggctcag attgaacgct ggcggcaggc ctaacacatg caagtcgagc        60
ggtagagaga agcttgcttc tcttgagagc ggcggacggg tgagtaatgc ctaggaatct       120
gcctggtagt gggggataac gttcggaaac ggacgctaat accgcatacg tcctacggga       180
gaaagcaggg gaccttcggg ccttgcgcta tcagatgagc ctaggtcgga ttagctagtt       240
ggtgaggtaa tggctcacca aggcgacgat ccgtaactgg tctgagagga tgatcagtca       300
```

```
cactggaact gagacacggt ccagactcct acgggaggca gcagtgggga atattggaca    360
atgggcgaaa gcctgatcca gccatgccgc gtgtgtgaag aaggtcttcg gattgtaaag    420
cactttaagt tgggaggaag ggttgtagat taatactctg caattttgac gttaccgaca    480
gaataagcac cggctaactc tgtgccagca gccgcggtaa tacagagggt gcaagcgtta    540
atcggaatta ctgggcgtaa agcgcgcgta ggtggtttgt taagttggat gtgaaatccc    600
cgggctcaac ctgggaactg cattcaaaac tgactgacta gagtatggta gagggtggtg    660
gaatttcctg tgtagcggtg aaatgcgtag atataggaag gaacaccagt ggcgaaggcg    720
accacctgga ctaatactga cactgaggtg cgaaagcgtg gggagcaaac aggattagat    780
accctggtag tccacgccgt aaacgatgtc aactagccgt tggaagcctt gagcttttag    840
tggcgcagct aacgcattaa gttgaccgcc tggggagtac ggccgcaagg ttaaaactca    900
aatgaattga cggggcccg cacaagcggt ggagcatgtg gtttaattcg aagcaacgcg    960
aagaacctta ccaggccttg acatccaatg aactttctag agatagattg gtgccttcgg   1020
gaacattgag acaggtgctg catggctgtc gtcagctcgt gtcgtgagat gttgggttaa   1080
gtcccgtaac gagcgcaacc cttgtcctta gttaccagca cgtaatggtg ggcactctaa   1140
```